(12) United States Patent
Moon et al.

(10) Patent No.: US 6,595,937 B1
(45) Date of Patent: Jul. 22, 2003

(54) BENT SPLINT AND METHOD OF MANUFACTURING THE SAME

(76) Inventors: Byong-Soon Moon, #963-11, Pyungsan-ri, Ungsang-up, Yangsan-city, Kyungsangnam-do 626-840 (KR); Byong-Hoon Moon, 107-910, Hyubsung APT., Booam-3 dong, Boosanji-ku, Boosan-city 614-093 (KR)

( * ) Notice: Subject to any disclaimer, the term of this patent is extended or adjusted under 35 U.S.C. 154(b) by 0 days.

(21) Appl. No.: 10/063,257

(22) Filed: Apr. 4, 2002

(51) Int. Cl.[7] .................................................. A61F 5/00
(52) U.S. Cl. ................. 602/5; 602/6; 602/20; 602/23; 602/26; 602/27
(58) Field of Search ................. 602/5, 6, 20, 23, 602/26–27

(56) References Cited

U.S. PATENT DOCUMENTS

| | | | |
|---|---|---|---|
| 3,592,189 A | * | 7/1971 | Bergen |
| 3,800,789 A | * | 4/1974 | Schloss |
| 4,349,016 A | * | 9/1982 | Glassman et al. |
| 4,489,716 A | * | 12/1984 | Blackwood et al. |
| 4,505,269 A | * | 3/1985 | Davies et al. |
| 5,941,263 A | * | 8/1999 | Bierman |
| 6,149,616 A | * | 11/2000 | Szelma et al. |
| 6,253,376 B1 | * | 7/2001 | Ritter |

* cited by examiner

*Primary Examiner*—Nicholas D. Lucchesi
*Assistant Examiner*—Lalita M. Hamilton
(74) *Attorney, Agent, or Firm*—Burns, Doane, Swecker & Mathis, L.L.P.

(57) ABSTRACT

The present invention relates to a bent splint used to wrap affected parts such as a fractured part and a ligament fractured part so that they do not move, and method of manufacturing the same. More particularly, the present invention relates to a bent splint that can facilitate a surgical operation by shaping the bent splint similar to an operation shape of a bent portion such as an elbow at a bent shape in which the wrinkles are not formed in the bent splint and that can increase an effect of a medical treatment by closely fixing the bent splint to the affected parts so that the splint does not float, and method of manufacturing the same. The bent splint for protecting/supporting the affected parts comprises an endoderm and an integument having a 'U' shape to which two bent plates having a horizontal section and a vertical section are adhered by an adhering means, the endoderm and integument having a bent portion for allowing an angle to be formed at its central portion; and a core being a sandwiched fabric in which a plurality of split fabrics are formed between the two fabric surfaces, wherein an outer circumference portion of the two bent plates having the horizontal section and the vertical section is adhered by an adhering means, so the cross section of the circumference portion is a 'U' shape, wherein a bent portion has an angle at its central portion, the endoderm and the integument are applied with a solidification solution such as polyurethane or gypsum, the core is inserted between the endoderm and an integument.

10 Claims, 7 Drawing Sheets

BENT SPLINT AND METHOD OF MANUFACTURING THE SAME

BACKGROUND OF INVENTION

1. Field of the Invention

The invention relates generally to a bent splint used to wrap affected parts such as a fractured joint or bone and a damaged ligament so that they do not move, and method of manufacturing the same. More particularly, the present invention relates to a bent splint that can facilitate recovery from a surgical operation by shaping the bent splint similar to an operation shape of a bent portion such as an elbow at a bent shape in which wrinkles are not formed in the bent splint and that can increase an effect of a medical treatment by closely fixing the bent splint to the affected parts so that the splint does not float, and method of manufacturing the same.

2. Description of the Prior Art

Generally, a splint for use in orthopedic surgery is used to partially or entirely firmly wrap fractured joints, broken bones, extension of a ligament and fractured muscular organization so that they can be firmly support/fixed.

At this time, it is required that materials used for the splint be flexible enough to shape the curved damaged parts and be adequate in solidification time or operation time. Further, it is required that the materials have a mechanical strength sufficient enough to maintain its structure. A method that has been widely used as splints meeting these requirements include a method of wrapping bandages on which gypsum material is applied to the affected parts. The gypsum bandage has been widely used as the bent splint since it can easily form the shape of the curved affected parts due to its flexible property before solidification, has adequate solidification time and operation time, and has a high mechanical strength after solidification. This gypsum bandage, however, requires much time to wrap the wounded parts because it must be wrapped on the affected parts in a sufficient thickness.

In order to solve this problem, there has been proposed a material for a splint being textiles such as gypsum bandage, glass fiber or synthetic fiber textiles is immersed into polyurethane resin for wet solidification (1 liquid phase) and is then folded 8–10 times. Thus, there is an advantage that this splint can reduce the use time. This splint is shaped with curve along the curved angle of humans' curved parts such as elbow, knee, heel, etc., since it is textiles formed in a rectangular shape. Thus, there is a disadvantage that wrinkled portions inevitably occur at the curved parts. Further, the splint lacks in the shaping capability closely wrapping the affected parts depending on the curved shapes from the affected parts, for example, the thickness of the wrist and ankle, the thickness of the ankle and calf, etc. In this case, the splint get loose from the affected parts and thus does not firmly support the affected parts, thus adversely affecting curing of the operation portion such as broken parts.

In order to solve this problem, there has been proposed a splint made of a thermoplastic resin. The splint is molded to have the cross section of a "U" shape and a "L" shape and has an endoderm attached as a sponge. At this time, the splint is molded to be an "L" shape. As the cross-sectional view of the splint is a "U" shape, it must be made soft at the temperature of about 90° C. in the oven in order for the splint to be closely adhered to the affected parts. The soft splint must be then attached to the affected parts along the curved parts of the affected parts by hands. During this operation, the soft splint of a thermoplastic resin becomes cool. Thus, the splint could not be completely attached to the affected parts once. Therefore, the splint must be made soft into the oven more than once. In addition, the splint must get cool for about 20 minutes after the shaping. Thus, there are problems that the operation is inconvenient and a lot of time is required.

SUMMARY OF INVENTION

The present invention is contrived to solve these problems and an object of the present invention is therefore to provide a bent splint capable of facilitating an operation and increasing an effect of the operation, in such a way that the splint is shaped to be a bent state like an operation shape in which wrinkles are not formed and the splint can be thus adhered to the affected parts so that the splint does not get loose, and method of manufacturing the same.

In order to accomplish the above object, a bent splint for protecting/supporting the affected parts according to the present invention, comprises an endoderm and an integument having an "U" shape to which two bent plates having a horizontal section and a vertical section are adhered by an adhering means, the endoderm and integument having a bent portion for allowing an angle to be formed at its central portion; and a core being a sandwiched fabric in which a plurality of split fabrics are formed between the two fabric surfaces, wherein an outer circumference portion of the two bent plates having the horizontal section and the vertical section is adhered by an adhering means, so the cross section of the circumference portion is a "U" shape, wherein a bent portion has an angle at its central portion, the endoderm and the integument are applied with a solidification solution such as polyurethane or gypsum, the core is inserted between the endoderm and an integument.

The bent plate is processed within a mold along the shape of the splint by means of an ultrasonic wave, so that the angle of the horizontal section 1a and the vertical section 1b can be maintained. Therefore, the cut cross section is smooth, there occur no wrinkles and loose fabrics can be prevented.

BRIEF DESCRIPTION OF DRAWINGS

The aforementioned aspects and other features of the present invention will be explained in the following description, taken in conjunction with the accompanying drawings, wherein:

FIG. 4a~FIG. 4d illustrate processes of manufacturing the bent splint according to the present invention;

FIG. 5a~FIG. 5c illustrate core built into the bent splint according to the present invention;

DETAILED DESCRIPTION

The present invention will be described in detail by way of a preferred embodiment with reference to accompanying drawings.

Referring now to FIGS. 1, 2, 3 and 4, an endoderm 2, an integument 3 and core 4 being bent plate constituting a bent splint 100 according to the present invention are bent means. The bent plates are cut to have a rectangular or given angle having horizontal sections 1a, 1a' and vertical sections 1b, 1b' by means of a molding cutter or an ultrasonic processing. The cut bent plates are the endoderm 2, integument 3 and core 4 in which rectangular or given angle having the horizontal sections 1a, 1a' and the vertical sections 1b, 1b' similar to the operation shape. The core 4 is intervened between the endoderm 2 and the integument 3 and is intervened by an ultrasonic wave thermal melting processing or seaming process. The endoderm 2 contacts the affected parts and is made of woven fabric, cotton or sponge. Also, a material for the integument 3 is exposed outside and is made of woven fabric or cotton having the durability. The endoderm 2 and the integument 3 each include two sheets of bent plates 5, 5', which are then seamed to an outer circumference portion 6 by an ultrasonic wave process or seaming process.

Figure 1:
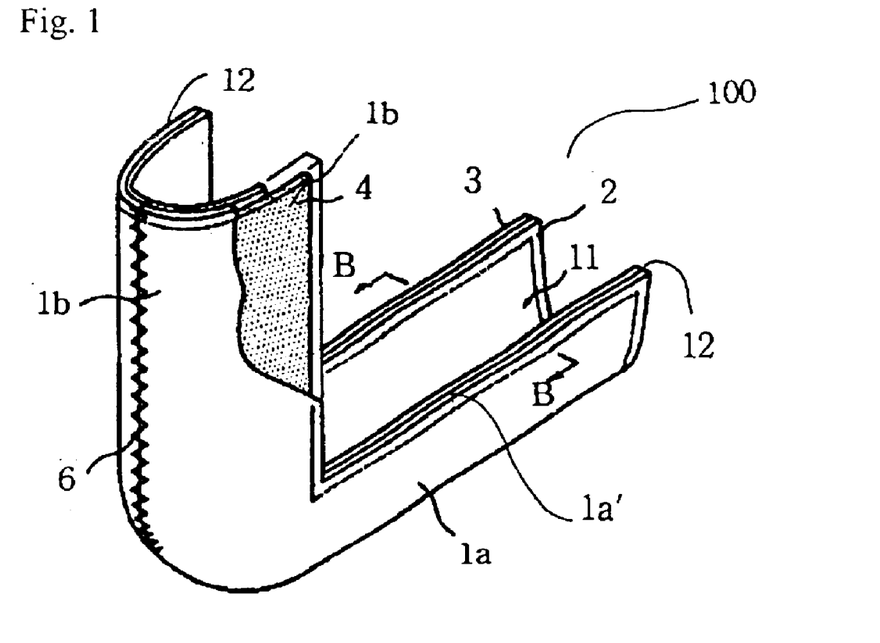
FIG. 1 is a perspective view of a partially cut-away bent splint.
Figure 2:
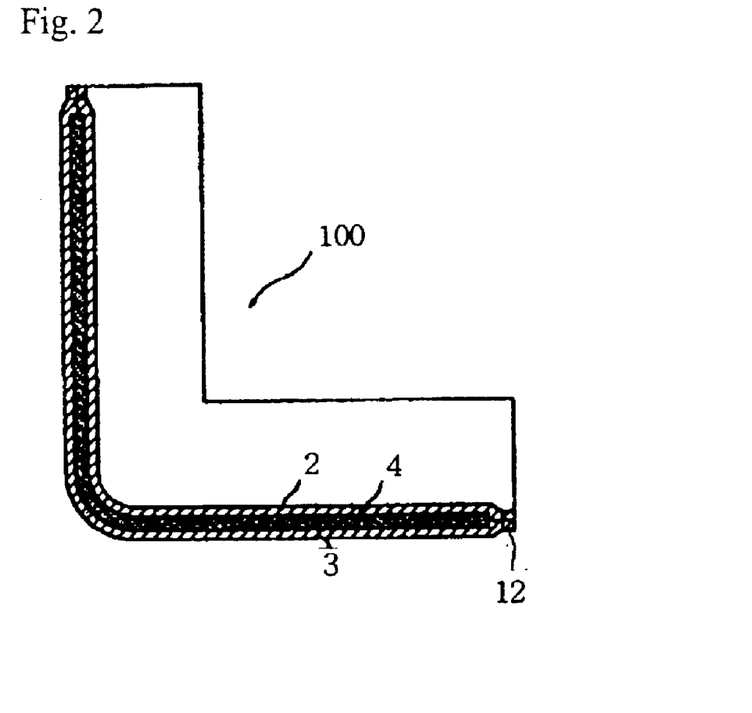
FIG. 2 is a longitudinal cross-section view of the bent splint in FIG. 1.
Figure 3:
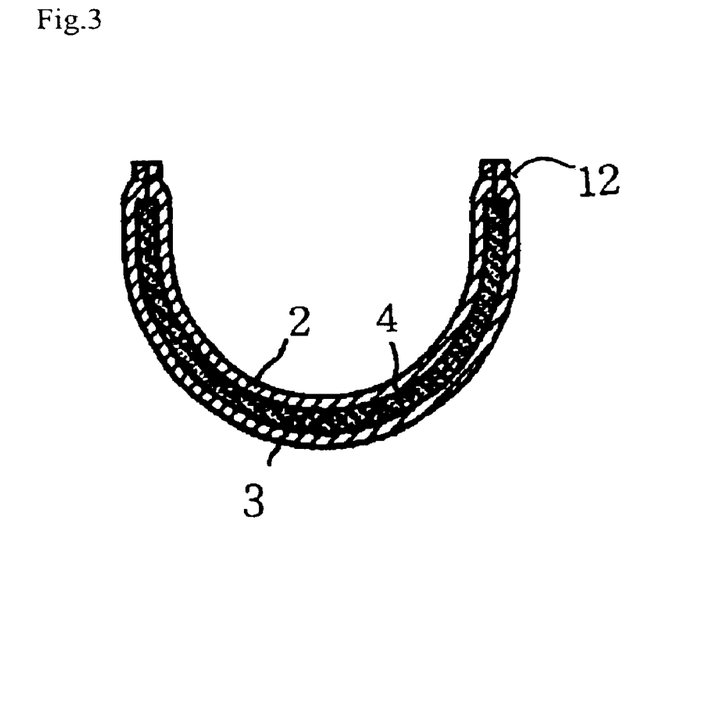
FIG. 3 is a cross-sectional view of the bent splint taken along line "B—B" in FIG. 1.
Figure 4A:
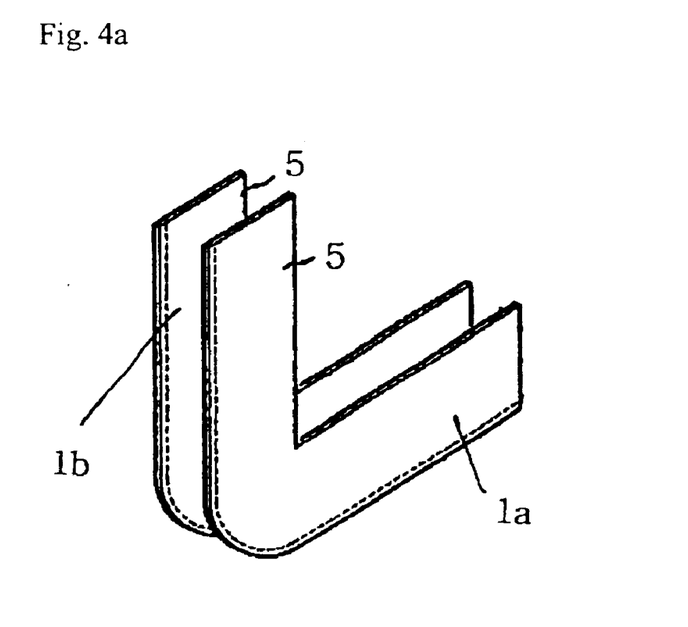
Figure 4B:
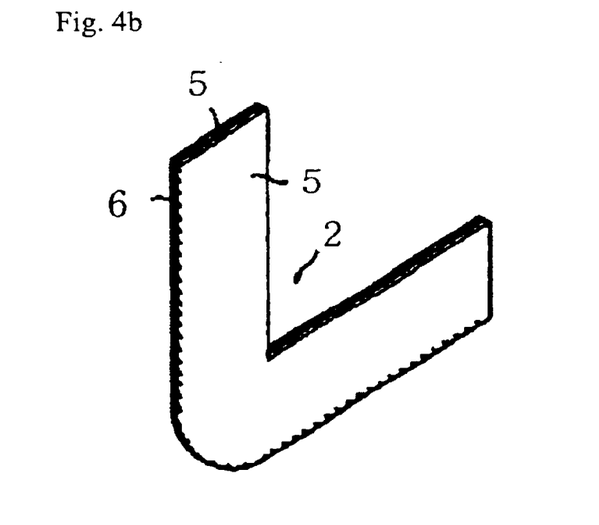
Figure 4C:
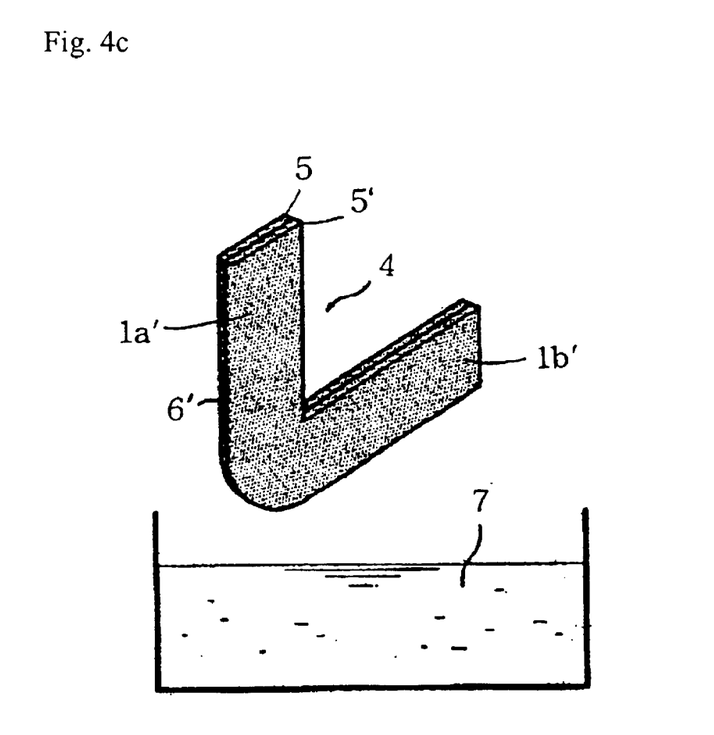
Figure 4D:
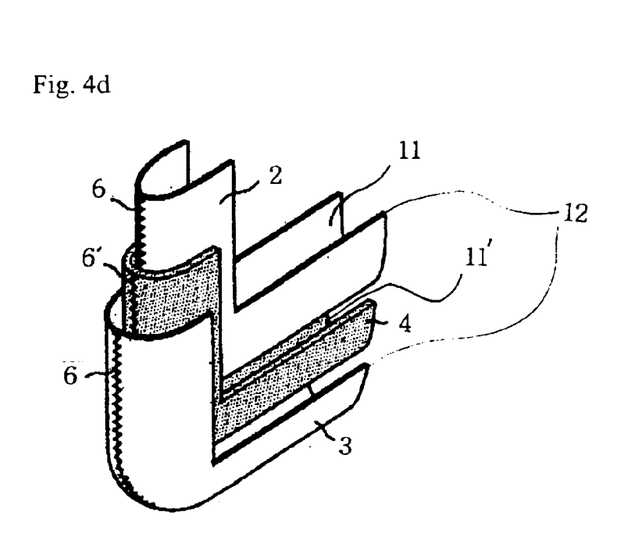
Figure 5A:
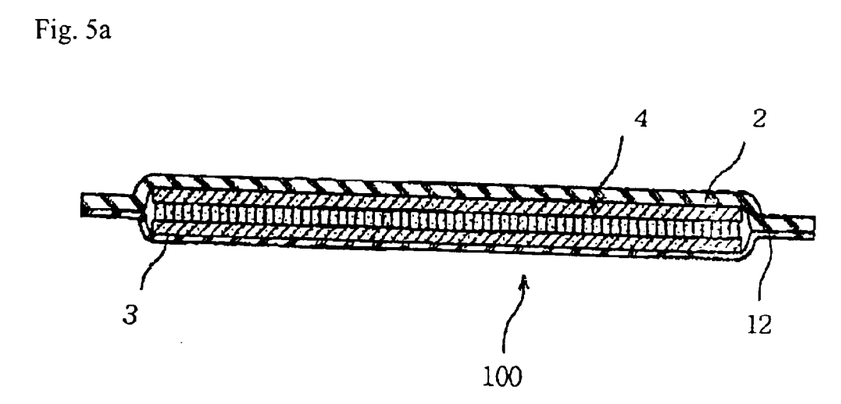
Figure 5B:
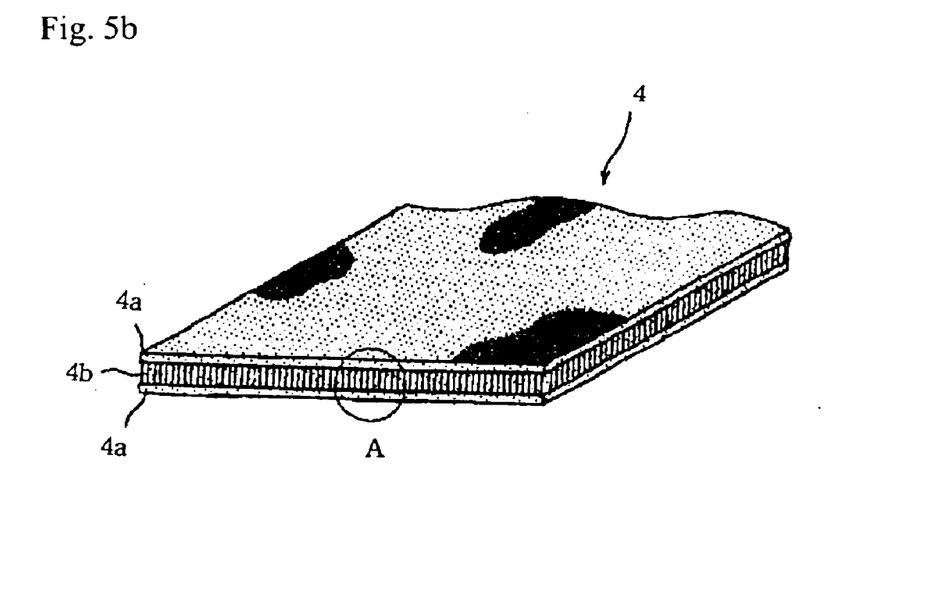
Figure 5C:
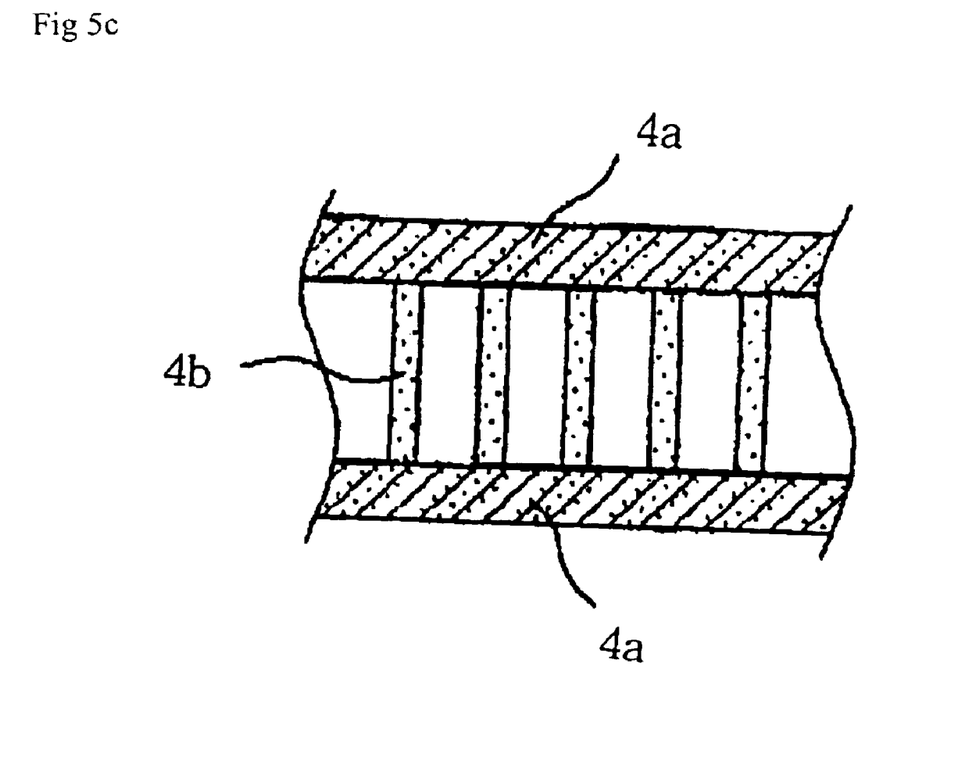

Referring now to FIGS. 4 and 5, the core 4 is intervened between the endoderm 2 and the integument 3, as shown in FIG. 5a–FIG. 5c. The core 4 includes woven fabrics, cotton, glass fiber, synthetic fiber woven fabrics or a sandwiched fabric having two surfaces 4a and a plurality of split fabrics 4b for connecting/supporting the two surfaces, as a basic material. FIG. 5c is an expanded drawing of a portion 'A' in FIG. 5b. The cut core 4 is immersed into a solidification solution 7 such as polyurethane resin for wet solidification type (1 liquid phase) or gypsum liquid and is then applied to the endoderm 2 and the integument 3, as shown in FIG. 4c. The core 4 shown in FIG. 5 is intervened between the endoderm 2 and the integument 3, as shown in FIG. 4d, so that the outer circumferences 12 of the endoderm 2 and the integument 3 are integrally adhered. The outer circumference 12 is thermally melted or seamed by a common ultrasonic wave processing or adhered by a tape.

The bent splint 100 formed as above has the endoderm 2, the integument 3 and the core 4 integrally formed. The bent splint is vacuum-packaged in order for the solidification solution 7 not to dry.

Referring to FIG. 4a~FIG. 4d, there are sequential processes of manufacturing the bent splint according to one embodiment of the present invention.

Referring to FIG. 4a, woven fabrics or cotton, sponge, glass fiber or synthetic fiber textiles being materials for the endoderm 2 and the integument 3, are cut within a mold to have a rectangular shape forming a given angle having a horizontal section 1a and a vertical section 1b using a mold along with the shape of the operation by means of an ultrasonic wave processing or a mold cutter. There are shown two sheets of the bent plate 5 that is cut by a mold cutter.

Referring to FIG. 4b, the seamed portions of the two sheets of the bent plate 5 and the outer circumference portion 6 are seamed or adhered by an ultrasonic wave processing. If they are unfolded, the cross section of the bent splint is a 'U' shape. The splint totally has a 'L' shape.

By reference to FIG. 4c, the core 4 is made of a sandwiched fabric having two surfaces 4a and a plurality of split fabrics 4b for connecting/supporting the two surfaces, as a basic material. The core 4 may be formed of sandwiched textiles or woven fabric, cotton, sponge, glass fiber and synthetic fiber textiles is made by the same method to the endoderm and the integument. The core 4 include two sheets of bent plates 5' having a rectangular angle or a given angle having a horizontal sections 1a' and a vertical section 1b'. A seaming portion 6' of the two sheets of the bent plates are seamed or thermally melt by an ultrasonic wave processing. Thus, if they are unfolded, the cross section of them have a 'U' shape and the entire shape has a 'L' shape. The core 7 is immersed into a solidification solution 7 such as gypsum resin or polyurethane resin.

Referring now to FIG. 4d, the core 4 to which the solidification solution 7 is applied is inserted between the endoderm 2 and the integument 3. The core 4 is then seamed to the endoderm 2 and the integument 3 or is adhered by an ultrasonic wave processing, thus forming a bent splint 100 as in FIG. 1.

As above, the bent splint 100 of the present invention includes the endoderm 2, the integument 3 and the core 4 to which encounter sections 6,6' of the two sheets of the bent plates 5,5' having a rectangular angle or a given angle are attached.

Figure 6:
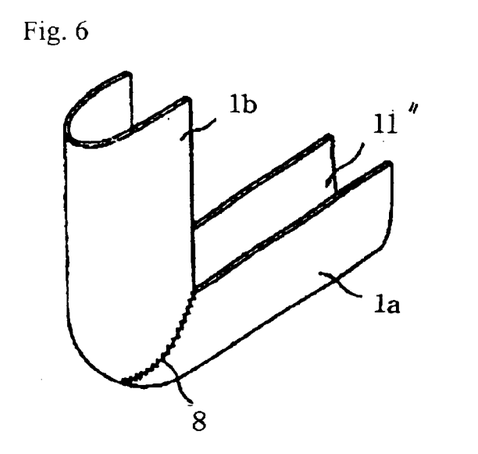
FIG. 6 shows another embodiment of a bent means.
Figure 7:
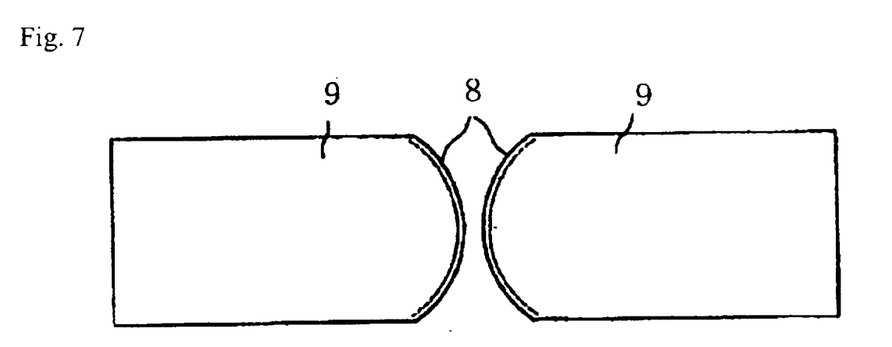
FIG. 7 is an unfolded view of the bent means in FIG. 6.

FIG. 6 and FIG. 7 show process of manufacturing the endoderm 2, the integument 3 and the core 4 as bent plates according to another embodiment of the present invention. Materials for the endoderm 2, the integument 3 and the core 4 are cut within a mold by means of a mold cutter or an ultrasonic wave process, so that two sheets of plates 9 one ends of which have arc shapes 8 are formed. Then, the central portion of the arc shape 8 is bent and the arc shape edges are seamed, forming the endoderm 2, the integument 3 and the core 4. The endoderm 2, the integument 3 and the core 4 having the cross sections of U shape 11" as lines 'B—B' in FIG. 1 can be produced.

Figure 8:
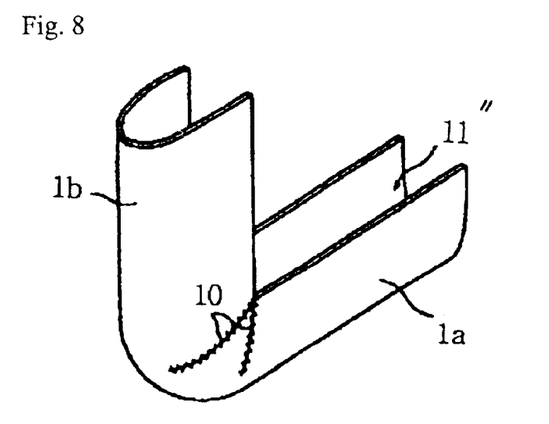
FIG. 8 shows a still another embodiment of a bent means.
Figure 9:
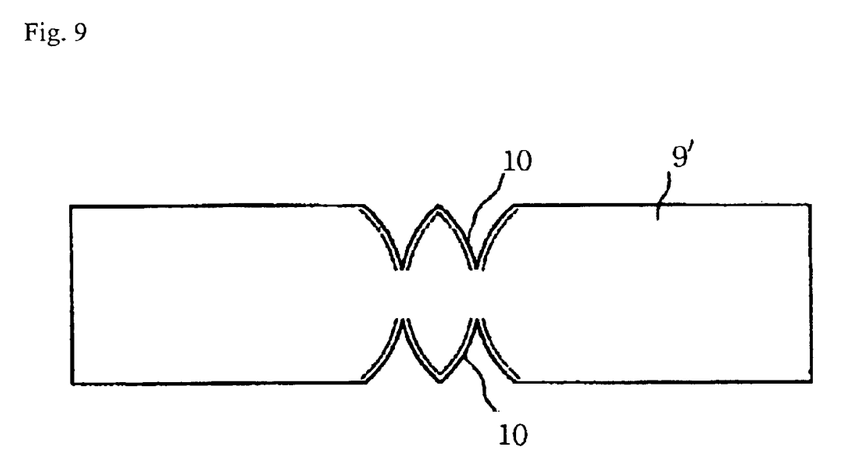
FIG. 9 is an unfolded view of the bent means in FIG. 8.

FIG. 8 and FIG. 9 show process of manufacturing the endoderm 2, the integument 3 and the core 4 as bent plates according to still another embodiment of the present invention. Materials for the endoderm 2, the integument 3 and the core 4 are cut within a mold by means of a mold cutter or an ultrasonic wave process, so that one sheet of plate 9'. The plate 9' is cut to have tacking sections 10' having a 'W' shape at its both ends. The central portion of the plate 9' is bent and the tacking sections 10' are seamed, forming the endoderm 2, the integument 3 and the core 4. The endoderm 2, the integument 3 and the core 4 having the cross sections of U shape 11' as lines 'B—B' in FIG. 1 can be produced.

The bent splint 100 includes the core 4 being a fabric such as FIG. 5a–FIG. 5c applied between the endoderm 2 and the integument 3 by means of solidification solution 7 such as polyurethane resin or gypsum solution.

The shape and angle of the bent splint 100 is bent in advance similar to the operation state. The core includes a plurality of the split fabrics for fixing the surface fabrics at upper and lower sides. A plurality of through-holes are formed between the split fabrics. Therefore, when the bent splint 100 is shaped in line with the shape of the affected parts, the through-holes formed between the splint fabrics of the core has a resilient force, so that it can itself receive variations in the curvature along the shape of the affected parts.

Therefore, there are no any wrinkles on the endoderm 2 and the integument 3 integrally formed with the core, as well as on the surface of the core 4.

In addition, the operation is simple since the range of controlling the range is narrow using the bent splint. Further, the affected parts can be closed to the bent splint so that the wrinkles such as conventional ones are not formed.

If the bent splint 100 is applied to the affected parts and surrounds/fixes the integument 3 of the bent splint 100, the core 4 is firmly solidified by the solidification solution 7 in 3–4 minutes, so that the fractured parts do not move.

As mentioned above, the bent splint 100 of the present invention is a splint in advance shaped similar to human's curved parts such as elbow, knee and heel. Thus, the splint can be closely adhered to the fractured parts or the affect parts since there are no wrinkles in the bent portions. Therefore, the present invention has outstanding advantages that it can reduce the curing time, increase the curing effect, and omit a process of bending up the bent portion.

The present invention has been described with reference to a particular embodiment in connection with a particular application. Those having ordinary skill in the art and access to the teachings of the present invention will recognize additional modifications and applications within the scope thereof.

It is therefore intended by the appended claims to cover any and all such applications, modifications, and embodiments within the scope of the present invention.

What is claimed is:

1. A bent splint for protecting/supporting the affected parts, comprising:

endoderm and integument the cross section of which are a 'U' and each having bent sections having a rectangular angle or a given angle, said endoderm and integument are formed by adhering encounter sections of two bent plates having a rectangular or a given angle having a horizontal section and a vertical section; and a core having sandwich textiles having a plurality of fabrics between two fabric surfaces and formed by adhering encounter sections of two bent plates having a rectangular or a given angle having a horizontal section and a vertical section;

wherein the cross section of the core is a 'U' shape, the central portion of the core has a bent portion having a rectangular angle or a given angle, and internal and outer surfaces of the core are applied with polyurethane for wet dry or a solidification solution, wherein the core is inserted between the endoderm and an integument and the encounter section in the endoderm and integument are adhered.

2. The bent splint as claimed in claim 1, wherein the endoderm and the integument are formed of one of woven fabrics, cotton and sponge, and the core is formed of one of gypsum bandage, woven fabrics, glass fiber, synthetic fiber woven fabrics and sandwiched fabrics.

3. The bent splint as claimed in claim 1, wherein the adhering means is seamed or thermally molt by means of an ultrasonic wave processing.

4. The bent splint as claimed in claim 1, wherein the bent plates include two sheets of plates one end of which have arc sections, have a 'U' shape by adhering the arc section and also have a bent portion having a given angle.

5. The bent splint as claimed in claim 1, wherein said bent plate includes a lacking portion of a 'W' shape at both ends at the central portion of one sheet of a plate body, has a 'U' shape by means of adhesion of the lacking portion and an bent portion having an angle.

6. A method of manufacturing a splint for wrapping/supporting the affected parts, comprising the steps of:

cutting two sheets of bent plates to have a rectangular angle or a given angle having a horizontal section and a vertical section along the shape of an operation portion by means of a mold cutter or an ultrasonic wave processing;

adhering encounter section portions of the two bent plates having a rectangular angle or a given angle including the horizontal section and the vertical section to produce an endoderm and an integument each having the cross section of a 'U' shape;

adhering encounter sections of the two sheets of bent plates made of sandwich fabrics in which a plurality of split fabrics are formed between the two fabric surfaces and having a rectangular angle or a given angle including a horizontal section and a vertical section to form a core the cross section of which is a 'U' shape;

immersing the core into a solidification solution made of polyurethane resin or gypsum solution to apply the endoderm and the integument with the solidification solution; and inserting the core between the endoderm and the integument and adhering the outer circumference portion by means of an adhering means.

7. The method as claimed in claim 6, wherein the endoderm and the integument are formed of one of woven fabrics, cotton and sponge, and the core is formed of one of gypsum bandage, woven fabrics, glass fiber, synthetic fiber woven fabrics and sandwiched fabrics.

8. The method as claimed in claim 6, wherein the two sheets of the bent plates as the adhering means are overlapped and then seamed or thermally-melt by an ultrasonic wave process so that a seamed portion can be formed in the outer circumference portion.

9. The method as claimed in claim 7, wherein one end of the bent plates are two sheets of plate bodies of an arc section, wherein the cross section of the bent plates has a 'U' shape by joining the arc section, and has a bent portion having an angle.

10. The method as claimed in claim 7, wherein the bent plate has a tacking portion of a 'W' shape on both ends at the central portion of one sheet of a plate body, has a 'U' shape by means of joining of the tacking portion and has a bent portion having an angle.

\* \* \* \* \*

UNITED STATES PATENT AND TRADEMARK OFFICE
CERTIFICATE OF CORRECTION

PATENT NO.     : 6,595,937 B1
DATED          : July 22, 2003
INVENTOR(S)    : Byong-Soon Moon et al.

It is certified that error appears in the above-identified patent and that said Letters Patent is hereby corrected as shown below:

<u>Title page,</u>
Item [76], change the second listed inventor's name from "Byong-Hoon Moon" to
-- Young-Hoon Moon --.

Signed and Sealed this

Twenty-fifth Day of November, 2003

JAMES E. ROGAN
*Director of the United States Patent and Trademark Office*